United States Patent [19]

Listemann et al.

[11] Patent Number: 5,710,191
[45] Date of Patent: Jan. 20, 1998

[54] HYDROXYMETHYL QUINUCLIDINE CATALYST COMPOSITIONS FOR MAKING POLYURETHANE FOAMS

[75] Inventors: Mark Leo Listemann, Whitehall; Kristen Elaine Minnich, Allentown; Brian Eugene Farrell, Fogelsville; Lisa Ann Mercando, Pennsburg; Michael John Kimock, Kutztown; James Dudley Nichols, Fogelsville, all of Pa.

[73] Assignee: Air Products and Chemicals, Inc., Allentown, Pa.

[21] Appl. No.: 647,159

[22] Filed: May 21, 1996

Related U.S. Application Data

[63] Continuation-in-part of Ser. No. 463,154, Jun. 5, 1995, abandoned.

[51] Int. Cl.[6] .................. C08G 18/20; C08J 9/04; C07D 251/34; C07C 269/02
[52] U.S. Cl. ............ 521/118; 502/167; 521/129; 521/155; 521/164; 521/166; 521/170; 521/902; 528/49; 528/54; 528/73; 528/74; 544/193; 544/222; 546/133; 560/24; 560/25; 560/26; 560/115; 560/157; 560/158; 560/355; 560/358
[58] Field of Search ................. 521/115, 116, 521/118, 129, 155, 164, 170, 902, 166; 528/49, 54, 73, 74; 544/193, 222; 560/24, 25, 26, 115, 158, 157, 355, 358; 502/167; 546/133

[56] References Cited

U.S. PATENT DOCUMENTS

| | | | |
|---|---|---|---|
| 3,035,021 | 5/1962 | Treacher et al. | 521/128 |
| 4,186,040 | 1/1980 | Aron et al. | 149/19.4 |
| 4,546,185 | 10/1985 | Bondiou et al. | 546/133 |
| 4,590,223 | 5/1986 | Arai et al. | 521/118 |
| 4,894,179 | 1/1990 | Santori et al. | 252/189 |
| 4,925,942 | 5/1990 | Götz et al. | 546/133 |
| 4,957,944 | 9/1990 | Schiffauer et al. | 521/115 |
| 5,071,809 | 12/1991 | Casey et al. | 502/155 |
| 5,143,944 | 9/1992 | Savoca et al. | 521/129 |
| 5,166,223 | 11/1992 | Savoca et al. | 521/103 |
| 5,194,609 | 3/1993 | Savoca et al. | 544/193 |
| 5,233,039 | 8/1993 | Listemann et al. | 544/193 |
| 5,238,894 | 8/1993 | Savoca et al. | 502/167 |
| 5,356,942 | 10/1994 | Savoca et al. | 521/103 |

OTHER PUBLICATIONS

G. Oertel, ed. "Polyurethane Handbook" Hanser Publishers, Munich, 1985, pp. 82, 84.

H.J. Fabris, "Advances in Urethane Science and Technology", vol. 6, Technomic Publishing Co., Westport, CT, 1978, pp. 173-179.

*Primary Examiner*—Rabon Sergent
*Attorney, Agent, or Firm*—Michael Leach; William F. Marsh

[57] ABSTRACT

A method for preparing a polyurethane foam which comprises reacting an organic polyisocyanate and a polyol in the presence of a blowing agent, a cell stabilizer and a catalyst composition comprising at least one compound of either of the following formulas IA and IB:

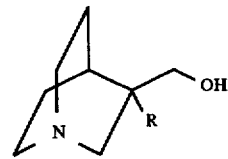

IA

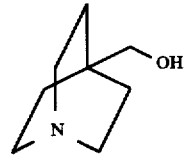

IB where R is hydrogen, methyl or hydroxymethyl. The preferred catalysts comprise 3-hydroxymethyl quinuclidine, 3-methyl-3-hydroxymethyl quinuclidine and 4-hydroxymethyl quinuclidine.

16 Claims, No Drawings

HYDROXYMETHYL QUINUCLIDINE CATALYST COMPOSITIONS FOR MAKING POLYURETHANE FOAMS

CROSS-REFERENCE TO RELATED APPLICATION

The present application is a continuation-in-part of application Ser. No. 08/463,154 filed Jun. 5, 1995, abandoned.

TECHNICAL FIELD OF THE INVENTION

The present invention relates to tertiary amine catalysts for catalyzing the urethane reaction in making polyurethane foam.

BACKGROUND OF THE INVENTION

Polyurethane foams are widely known and used in automotive, housing and other industries. Foam is generally referred to as rigid, microcellular, or flexible. Typically, in the preparation of polyurethane foams, a tertiary amine catalyst is used to accelerate the reaction of the polyisocyanate with water to generate carbon dioxide as a blowing agent and to accelerate the reaction with polyols to promote gelling. Tertiary amines generally are malodorous and offensive, and many have high volatility due to low molecular weight. Release of tertiary amine during foam processing may present significant safety and toxicity problems, and release of residual amines from consumer products is generally undesirable.

Amine catalysts which contain primary and/or secondary hydroxyl functionality typically have limited volatility and low odor when compared to related structures which lack this functionality. Furthermore, catalysts which contain hydroxyl functionality chemically bond into the urethane during the reaction and are not released from the finished product. Catalyst structures which embody this concept are typically of low to moderate activity and are designed to promote primarily the blowing (water-isocyanate) reaction.

U.S. Pat. No. 4,957,944 discloses certain dimethylamino alkyleneoxy isopropanols for use as a catalyst for preparing polyurethane foam.

U.S. Pat. No. 5,071,809 discloses tertiary amine catalysts containing secondary alcohol functionality for use in preparing polyurethane foams. The tertiary amines containing secondary alcohol functionality are prepared by reacting an olefinic nitrile with an aliphatic polyol having at least one secondary hydroxyl functionality, followed by reductive alkylation of the resulting cyanoalkylated polyol with a secondary aliphatic or cycloaliphatic amine, including those containing hetero atoms.

U.S. Pat. No. 4,590,223 discloses the preparation of tertiary amines containing secondary alcohols by reacting N-alkyl-piperazines with an alkyleneoxide.

Secondary alcohol functionality is preferred in these structures because the catalysts exhibit a desirable balance between their promotion of the water-isocyanate reaction and their own reactivity with isocyanates. In contrast, catalysts which contain primary alcohols react rapidly with isocyanates and thus high use levels are required. Catalysts which contain tertiary alcohols react slowly with isocyanates, but the urethanes which are formed from the tertiary alcohols have poor thermal stability. See G. Oertel, ed. "Polyurethane Handbook," Hanser Publishers, Munich, 1985, pp. 82, 84 and H. J. Fabris, "Advances in Urethane Science and Technology," Vol. 6, Technomic Publishing Co., Westport, Conn., 1978, pp. 173–179. These urethanes may degrade and release the catalysts at temperatures substantially below the decomposition temperature of the foam itself. The free amine could then accelerate foam decomposition.

A catalyst which strongly promotes the polyol-isocyanate (gelling) reaction is necessary for the manufacture of many polyurethane foams. Triethylenediamine (1,4-diazabicyclo [2.2.2.]octane) is widely used for this purpose. Quinuclidine (1-azabicyclo-[2.2.2.]octane) can also be used as a gelling catalyst, particularly when the polyol contains a preponderance of secondary hydroxyl groups (U.S. Pat. No. 3,036,021). Quinuclidine is more reactive than triethylenediamine for the production of polyurethane foams. Both triethylenediamine and quinuclidine are volatile materials which will not remain trapped in the foam.

U.S. Pat. No. 3,036,021 also discloses that 1-azabicyclooctanes and their alkyl, amino, hydroxyl, nitro, alkoxy and halogen derivatives can also be used as gelling catalysts, although no distinctions were made with regard to the effect of catalyst structure on activity or suitability for incorporation into a foam.

U.S. Pat. No. 4,186,040 discloses a solid, pyrotechnic composition for dissemination of 3-quinuclidinyl benzylete, the composition consisting essentially of 3-quinuclidinyl benzylete and an oxidizer incorporated in a solid foamed polyurethane binder. No information is provided on the utility of quinuclidinyl benzylete as a catalyst or as a TEDA replacement. Furthermore, quinuclidinyl benzylete does not remain trapped in the foam.

U.S. Pat. No. 5,143,944 discloses the use of 3-quinuclidinol and its alkoxylated derivatives, all of which contain secondary alcohols, as high activity, high selectivity gelling catalysts which will react with and remain trapped in the foam.

U.S. Pat. No. 4,546,185 discloses the synthesis of 3-hydroxymethyl quinuclidine for use as a pharmaceutical intermediate. No information concerning the utility of 3-hydroxymethyl quinuclidine as a polyurethane catalyst is provided.

SUMMARY OF THE INVENTION

The present invention provides a catalyst composition for catalyzing the trimerization of an isocyanate and/or the reaction between an isocyanate and a compound containing a reactive hydrogen, e.g., the urethane reaction for making polyurethane. The catalyst composition is a family of hydroxy-functional amines which comprises 3-hydroxymethyl quinuclidine (i.e., 3-hydroxymethyl-1-azabicyclo[2.2.2.]-octane) and 3-substituted derivatives of 3-hydroxymethyl quinuclidine, as represented by following formula 1A, and 4-hydroxymethyl quinuclidine (i.e., 4-hydroxymethyl-1-azabicyclo [2.2.2.]-octane), as represented by following formula IB:

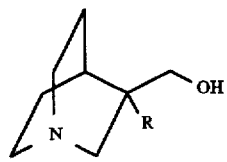

IA

3

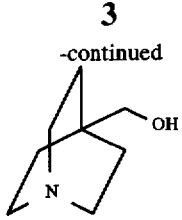

IB where R is hydrogen, methyl or hydroxymethyl.

As an advantage of the catalyst compositions, they strongly promote the polyolisocyanate (gelling) reaction and are subsequently incorporated into the polyurethane product.

Another embodiment of the present invention is a polyurethane foam prepared by reacting a polyisocyanate, a polyol, water, cell stabilizer and a catalyst composition which comprises at least one of the hydroxyl functional amines of the above formulas IA and IB.

DETAILED DESCRIPTION OF THE INVENTION

The catalyst compositions according to the invention can catalyze (i) the reaction between an isocyanate functionality and an active hydrogen-containing compound, i.e. an alcohol, an amine or water, especially the urethane (gelling) reaction to make polyurethanes and the blowing reaction of water with isocyanate to release carbon dioxide for making foamed polyurethanes, and (ii) the trimerization of the isocyanate functionality to form polyisocyanurates.

The polyurethane products are prepared using suitable organic polyisocyanates well known in the art including, for example, hexamethylene diisocyanate, phenylene diisocyanate, toluene diisocyanate ("TDI") and 4,4'-diphenylmethane diisocyanate ("MDI"). Especially suitable are the 2,4- and 2,6-TDIs individually or together as their commercially available mixtures. Other suitable isocyanates are mixtures of diisocyanates known commercially as "crude MDI", also known as PAPI, which contain about 60% of 4,4'-diphenylmethane diisocyanate along with other isomeric and analogous higher polyisocyanates. Also suitable are "prepolymers" of these polyisocyanates comprising a partially prereacted mixture of polyisocyanates and polyether or polyester polyols.

Illustrative of suitable polyols as a component of the polyurethane composition are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols; for example, among others, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane and like low molecular weight polyols.

In the practice of this invention, a single high molecular weight polyether polyol may be used. Also, mixtures of high molecular weight polyether polyols such as mixtures of di- and tri-functional materials and/or different molecular weight or different chemical composition materials may be used.

Useful polyester polyols include those produced by reacting a dicarboxylic acid with an excess of a diol, for example, adipic acid with ethylene glycol or butanediol, or reacting a lactone with an excess of a diol such as reacting caprolactone with propylene glycol.

In addition to the polyether and polyester polyols, the masterbatches, or premix compositions, frequently contain a polymer polyol. Polymer polyols are used in polyurethane foam to increase the foam's resistance to deformation, i.e. to increase the load-bearing properties of the foam. Currently, two different types of polymer polyols are used to achieve load-bearing improvement. The first type, described as a graft polyol, consists of a triol on which vinyl monomers are graft copolymerized. Styrene and acrylonitrile are the usual monomers of choice. The second type, polyurea modified polyols, is a polyol containing a polyurea dispersion formed by the reaction of a diamine and TDI. Since TDI is used in excess, some of the TDI may react with both the polyol and polyurea. This second type of polymer polyol has a variant called PIPA polyol which is formed by the in-situ polymerization of TDI and alkanolamine in the polyol. Depending on the load-bearing requirements, polymer polyols may compose 20–80% of the polyol portion of the masterbatch.

Other typical agents found in the polyurethane foam formulations include crosslinkers such as ethylene glycol, butanediol, diethanolamine, diisopropanolamine, triethanolamine and/or tripropanolamine; blowing agents such as water, methylene chloride, trichlorofluoromethane and the like; and cell stabilizers such as silicones.

A general polyurethane flexible foam formulation containing the catalyst composition according to the invention would comprise the following components in parts by weight (pbw):

| Flexible Foam Formulation | |
|---|---|
| | Parts by Weight |
| Polyol | 20–80 |
| Polymer Polyol | 80–20 |
| Silicone Surfactant | 1–2.5 |
| Blowing Agent | 2–4.5 |
| Crosslinker | 0.5–2 |
| Catalyst | 0.5–2 |
| Isocyanate Index | 92–115 |

The urethane catalyst composition comprises a 3-hydroxymethyl quinuclidine compound of the following general formula IA or 4-hydroxymethyl quinuclidine, or mixtures thereof:

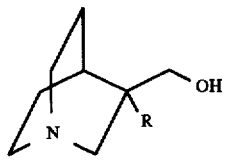

IA where R is a hydrogen, methyl or hydroxymethyl, preferably methyl.

Specific compositions include the following compounds:

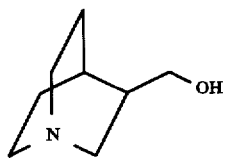

3-Hydroxymethyl Quinuclidine

The 3-hydroxymethyl quinuclidine may be prepared by the procedure of U.S. Pat. No. 4,546,185.

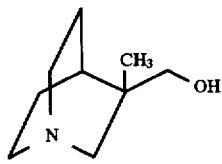

3-Methyl-3-Hydroxymethyl Quinuclidine

The 3-methyl-3-hydroxymethyl quinuclidine may be prepared by reacting ethylpyridine with formaldehyde to afford 2-methyl-2-(4-pyridyl)-1,3,-propanediol which is hydrogenated to 2-methyl-2-(4-piperidyl)-1,3-propanediol which in turn is cyclized to the quinuclidine product.

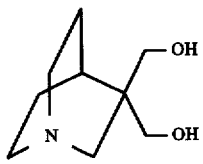

3-Bis(hydroxymethyl) Quinuclidine

The 3-bis(hydroxymethyl) quinuclidine may be prepared by reacting 4-picoline with formaldehyde to afford 2-hydroxymethyl-2-(4-pyridyl)-1,3-propanediol which is hydrogenated to 2-hydroxymethyl-2-(4-piperidyl)-1,3-propanediol which in turn is cyclized to the quinuclidine product.

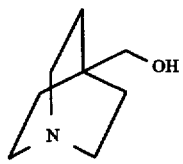

4-Hydroxymethyl Quinuclidine

The 4-hydroxymethyl quinuclidine may be prepared by a procedure similar to that in U.S. Pat. No. 5,190,953, but starting with isonipecotic acid ethyl ester which is available from Aldrich Chemicals.

The mixtures can be prepared by simply blending the desired amounts of the 3-hydroxymethyl quinuclidine compound(s) and/or 4-hydroxymethyl quinuclidine.

A catalytically effective amount of the catalyst composition is used in the polyurethane formulation. More specifically, suitable amounts of the catalyst composition may range from about 0.01 to 10 parts per 100 parts by weight polyol in the polyurethane formulation.

The catalyst compositions may also contain other tertiary amine, organotin and metal carboxylate urethane catalysts well known in the urethane art.

EXAMPLE 1

In this example a polyurethane foam was prepared in a conventional manner. The polyurethane formulation in parts by weight was:

| COMPONENT | PARTS |
|---|---|
| E-648 Polyol | 60 |
| E-519 Polyol | 40 |
| Water | 3.5 |
| Diethanolamine | 1.49 |
| DC 5043 | 1.5 |
| TDI 80 | 105 index |

The foam reactivity was measured using either 33 wt % 3-hydroxymethyl quinuclidine (3-HMQ) in dipropylene glycol or DABCO 33LV® catalyst (33 wt % triethylenediamine in dipropylene glycol) as gelling catalysts and DABCO® BL-11 catalyst [70 wt % bis(dimethylaminoethyl)ether in dipropylene glycol] as the blowing catalyst. The 3-HMQ was prepared according to U.S. Pat. No. 4,546,185. Table 1 sets forth conditions and results.

TABLE 1

| Catalyst | DABCO 33LV/ DABCO BL-11 | 3-HMQ/ DABCO BL-11 |
|---|---|---|
| Amount (mmoles) | 1.04/0.52 | 1.04/0.52 |
| Amount (pbw) | 0.35/0.12 | 0.44/0.12 |
| Top of Cup 1 (sec) | 12.9 | 13.8 |
| Top of Cup 2 (sec) | 37.2 | 39.0 |
| String Gel (sec) | 73.1 | 71.1 |
| Full Rise Time (sec) | 103.3 | 111.3 |

Times cited were from mixing of the polyol masterbatch with isocyanate. Top of Cup 1 represents the time required for the foam formulation to fill a 16 oz cup and is an indication of reaction initiation. Top of Cup 2 represents the time required for the foam formulation to fill a 1 gal cup in addition to the 16 oz cup mentioned above and is an indication of reaction progression. String Gel and Full Rise are further measures of reaction progression and provide some indication of extent of cure.

The advantage of 3-hydroxymethyl quinuclidine is that, when compared on an equimolar level, it provides an excellent reactivity match for triethylenediamine during the critical early stages of the foaming reaction, and is then incorporated into the polymer, as seen in the increased full rise time measurement. Furthermore, the amount of 3-hydroxymethyl quinuclidine can be increased to shorten the full rise time, but volatile emissions from the final product will not increase.

EXAMPLE 2

Synthesis of 4-Hydroxymethyl Quinuclidine

Ethyl isonipecotate (25 g; 0.159 mole) and 40 mL of dichloromethane were added to a 250 mL 3-neck round bottom flask equipped with a magnetic stir bar and an addition funnel under nitrogen. A solution of di-t-butyldicarbonate (34.7 g; 0.159 mole) and 40 mL of dichloromethane was added dropwise over a period of 2 hr. The reaction mixture was then allowed to stir for an additional 2 hr at room temperature. A yellow viscous liquid remained upon evaporation of the solvent. Distillation (100°–110° C., 2 mTorr) removed excess starting material, resulting in 92% yield of the t-BOC ester.

21.17 g of the t-BOC ester (82.3 mmole) was dissolved in 60 mL of tetrahydrofuran in a 250 mL 3-neck round bottom flask equipped with a magnetic stir bar. This solution was cooled to –40° C. and lithium diisopropyl amine (45 mL;

90.0 mmole) was added slowly under nitrogen. The reaction mixture was stirred for 1 hour at −15° C. The reaction mixture was then cooled to −40° C. and bromochloroethane (7.5 mL; 90.1 mmole) was added slowly and the mixture warmed to room temperature over the period of an hour. The reaction mixture was concentrated to a viscous orange oil via rotatory evaporation. The residue was taken up in diethyl ether (75 mL) and washed with 150 mL saturated sodium bicarbonate. The aqueous layer was then extracted with diethyl ether (2×50 mL). The combined ether layers were dried over sodium sulfate, filtered, and solvent evaporated to give an orange oil.

The orange oil was dissolved in dichloromethane (50 mL) and cooled to 0° C. in an ice bath. Trifluoroacetic acid was added dropwise under nitrogen and the reaction mixture slowly warmed to room temperature and stirred for 2 hours. The solution was then washed with 75 mL saturated potassium carbonate. The aqueous layer was extracted with dichloromethane (2×50 mL) and the organic layers were combined and dried over sodium sulfate. Removal of the solvent resulted in an orange oil which was dissolved in acetonitrile and refluxed for 2 hr. Evaporation of the acetonitrile resulted in an orange oil which was then partitioned between dichloromethane and aqueous sodium bicarbonate. Solvent evaporation and distillation resulted in a viscous liquid. Reduction was then performed on the viscous liquid with lithium aluminum hydride in tetrahydrofuran to produce 4-hydroxymethyl quinuclidine. This material was purified by column chromatography on silica gel, eluting with methanol, to yield a white solid in 39.5% yield.

EXAMPLE 3

This example compares the selectivities and activities of 3-hydroxymethyl quinuclidine and 4-hydroxymethyl quinuclidine with those of triethylenediamine, 3-quinuclidinol and 2-hydroxymethyl triethylenediamine.

The rate of isocyanate consumption as a function of time was measured using a formulation similar to that of Example 1, but containing monofunctional reactants. Reaction samples drawn at the indicated times were quenched with dibutylamine and analyzed by liquid chromatography. Catalyst selectivity is defined as the ratio of the rate of blowing (urea formation) to the rate of gelling (urethane formation). A selectivity of "one" means that the amounts of blowing and gelling are equal at that point in the reaction. A selectivity substantially below "one", for example about 0.3, is indicative of a strong gelling catalyst. A selectivity greater than "one" is indicative of a blowing catalyst. The catalysts were compared on an equimolar basis corresponding to a loading of 0.35 parts per hundred parts polyol of DABCO 33 LV catalyst in the polyurethane foam formulation in Example 1. Table 2 sets forth the results.

TABLE 2

| Catalyst | 0.5 | 1.0 | 1.5 | 2.0 | 3.0 | 4.0 | 6.0 | 8.0 |
|---|---|---|---|---|---|---|---|---|
| Triethylenediamine | | | | | | | | |
| Selectivity | 0.30 | 0.35 | 0.45 | 0.50 | 0.61 | 0.69 | 0.73 | 0.77 |
| % NCO Conversion | 14.2 | 28.9 | 44.0 | 50.3 | 64.1 | 71.6 | 79.9 | 83.6 |
| 3-Quinuclidinol | | | | | | | | |
| Selectivity | 0.33 | 0.43 | 0.51 | 0.57 | 0.67 | 0.70 | 0.70 | 0.70 |

Time (min) header for table 2.

TABLE 2-continued

| Catalyst | 0.5 | 1.0 | 1.5 | 2.0 | 3.0 | 4.0 | 6.0 | 8.0 |
|---|---|---|---|---|---|---|---|---|
| % NCO Conversion | 19.2 | 34.4 | 46.6 | 54.5 | 66.3 | 72.7 | 79.3 | 83.2 |
| 3-Hydroxymethyl Quinuclidine | | | | | | | | |
| Selectivity | 0.36 | 0.45 | 0.52 | 0.57 | 0.66 | 0.70 | 0.74 | 0.76 |
| % NCO Conversion | 23.1 | 39.4 | 49.6 | 55.9 | 65.1 | 70.1 | 75.4 | 79.4 |
| 4-Hydroxymethyl Quinuclidine | | | | | | | | |
| Selectivity | 0.34 | 0.40 | 0.44 | 0.48 | 0.55 | 0.60 | 0.68 | 0.69 |
| % NCO Conversion | 15.8 | 28.6 | 39.9 | 46.0 | 56.9 | 63.9 | 71.4 | 75.3 |
| 2-Hydroxymethyl Triethylenediamine* | | | | | | | | |
| Selectivity | 0.58 | 0.66 | 0.68 | 0.69 | 0.69 | 0.67 | 0.64 | 0.65 |
| % NCO Conversion | 5.3 | 10.9 | 15.7 | 21.3 | 28.4 | 37.1 | 47.8 | 54.8 |

*Run at twice the molar level of the first four catalysts.

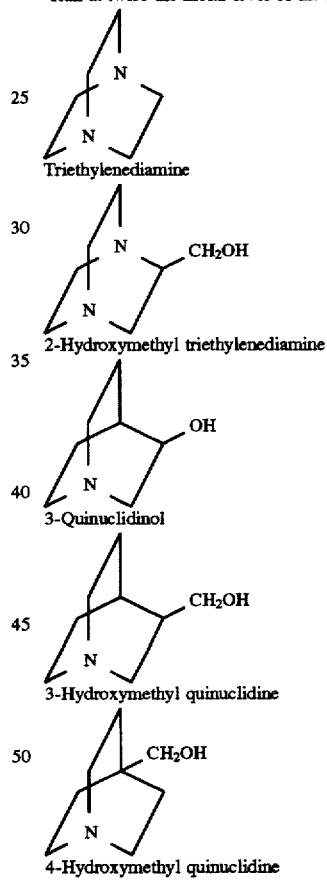

The uniqueness of the 3- and 4-hydroxymethyl quinuclidines is that these are the first high gelling selectivity, high activity tertiary amine catalysts which contain primary alcohol functionality and function as mole for mole replacements for industry standard triethylenediamine. The activity, as measured by % NCO conversion at 0.5 min, must increase in the order: triethylenediamine<3-quinuclidinol<3-hydroxymethyl quinuclidine and 4-hydroxymethyl quinuclidine to compensate for the incorporation of the catalyst into the polymer. The choice of primary alcohol containing structure is not obvious, because the related molecule 2-hydroxymethyl triethylenediamine shows both an initial selectivity which does not sufficiently favor gelling, and an activity which is substantially lower than that of triethylenediamine.

EXAMPLE 4

Synthesis of 3-Methyl-3-Hydroxymethyl Quinuclidine (MHMQ)

MHMQ is produced by a three-step process starting with 4-ethylpyridine and formaldehyde.

1. 2-Methyl-2-(4-pyridyl)-1,3-propanediol (MPyPD)

MPyPD is produced by the reaction of 4-ethylpyridine (167 g; 1.56 mole) and formaldehyde (93.6 g; 3.12 mole) [170 g formcel (55% formaldehyde/45% methanol)] in an autoclave at 140° C./400 psig (27 atm) nitrogen/3–5 hr. The excess 4-ethylpyridine, methanol and formaldehyde are removed by vacuum stripping at 75°–100° C.

2. 2-Methyl-2-(4-piperidyl)-1,3-propanediol (MPipPD)

The crude MPyPD product mixture is hydrogenated to produce MPipPD: MPyPD (30–40% solution in isopropanol or tetrahydrofuran) is reacted over 20–30% of 5% Rh/C (or 5% Ru/C) at 100°–130° C./1000 psig (68 atm) hydrogen/4–6 hr. MPipPD is purified by distillation (130°–150° C./1 torr) to remove all volatile materials.

3. 3-Methyl-3-Hydroxymethyl Quinuclidine (MHMQ)

MPipPD is cyclized to MHMQ by passing an aqueous solution of MPipPD over a fixed catalyst bed of strontium phosphate at 175°–250° C. MHMQ is purified by distillation at reduced pressure.

EXAMPLE 5

Synthesis of 3-Bis(hydroxymethyl) Quinuclidine (BHMQ)

BHMQ is produced by a three-step process starting with 4-picoline and formaldehyde:

1. 2-Hydroxymethyl-2-(4-pyridyl)-1,3-propanediol (HMPyPD)

HMPyPD is produced by the reaction of 4-picoline (93 g; 1.0 mole)] and formaldehyde (120 g; 4.0 mole) [218 g formcel (55% formaldehyde/45% methanol)] in an autoclave at 140°–160° C./400 psig (27 atm) nitrogen/6–10 hr. The excess 4-picoline, methanol and formaldehyde are removed by vacuum stripping at 75-100° C.

2. 2-Hydroxymethyl-2-(4-piperidyl)-1,3-propanediol (HMPipPD)

The crude HMPyPD product mixture is hydrogenated to produce HMPipPD: HMPyPD (30–40% solution in isopropanol or tetrahydrofuran) is reacted over 20–30% of 5% Rh/C at 100°–130° C./1000 psig (68 atm) hydrogen/4–6 hr. HMPipPD is purified via distillation (130°–150° C./1.0 torr) to remove all volatile materials.

3. 3-Bis(hydroxymethyl) Quinuclidine (BHMQ)

HMPipPD is cyclized to BHMQ by passing an aqueous solution of HMPipPD over a fixed catalyst bed of strontium phosphate at 175°–250° C. BHMQ is purified by recrystallization from ethyl acetate.

The prior art high activity amine gelling catalysts are fugitive in that they can escape from a foam during or after its manufacture. The present invention successfully incorporates primary alcohol functionality into high activity gelling catalysts which display activity similar to that of TEDA, the industry standard. The primary alcohol functionality lowers the volatility of the catalysts of the invention and prevents their escape from the finished foam product through the chemical reaction with the foam itself.

The prior art does not indicate that 3-hydroxymethyl quinuclidine and 4-hydroxymethyl quinuclidine would be expected to have activity very similar to that of TEDA. An activity match is desirable so that the catalysts for the present invention can be easily employed and accepted by industry as drop-in replacements for TEDA.

STATEMENT OF INDUSTRIAL APPLICATION

The present invention provides compositions for catalyzing the urethane reaction and preparing urethane products, especially polyurethane foam products.

We claim:

1. In a method for catalyzing the trimerization of an isocyanate and/or its reaction with an active hydrogen-containing compound, the improvement which comprises using as a catalyst at least one compound of formulas IA and IB:

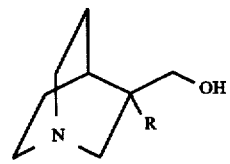

IA

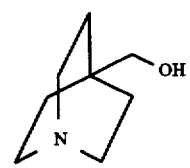

IB where R is hydrogen, methyl or hydroxymethyl.

2. The method of claim 1 in which the catalyst is 3-hydroxymethyl quinuclidine.

3. The method of claim 1 in which the catalyst is 4-hydroxymethyl quinuclidine.

4. The method of claim 1 in which the catalyst is 3-methyl-3-hydroxymethyl quinuclidine.

5. In a method for preparing a polyurethane foam which comprises reacting an organic polyisocyanate and a polyol in the presence of a blowing agent, a cell stabilizer and a catalyst composition, the improvement which comprises employing a catalyst composition comprising at least one compound of the following formulas IA and IB:

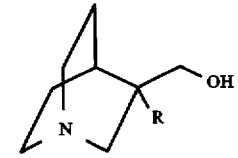

IA

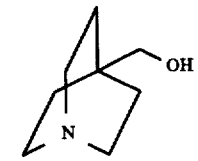

IB where R is hydrogen, methyl or hydroxymethyl.

6. The method of claim 5 in which the catalyst composition also contains at least one other tertiary amine, organotin or metal carboxylate urethane catalyst.

7. The method of claim 5 in which the catalyst composition comprises 3-hydroxymethyl quinuclidine.

8. The method of claim 7 in which the catalyst composition also contains at least one other tertiary amine, organotin or metal carboxylate urethane catalyst.

9. The method of claim 5 in which the catalyst composition comprises 4-hydroxymethyl quinuclidine.

10. The method of claim 9 in which the catalyst composition also contains at least one other tertiary amine, organotin or metal carboxylate urethane catalyst.

11. The method of claim 5 in which the catalyst composition comprises 3-methyl-3-hydroxymethyl quinuclidine.

12. The method of claim 11 in which the catalyst composition also contains at least one other tertiary amine, organotin or metal carboxylate urethane catalyst.

13. In a polyurethane foam composition which comprises an organic polyisocyanate, a polyol, a blowing agent, a cell stabilizer and a catalyst composition, the improvement which comprises a catalytically effective amount of a catalyst composition comprising 3-hydroxymethyl quinuclidine, 3-methyl-3-hydroxymethyl quinuclidine or 4-hydroxymethyl quinuclidine.

14. The composition of claim 13 which comprises a catalyst composition comprising 0.1 to 10 parts 3-hydroxymethyl quinuclidine and at least one other tertiary amine, organotin or metal carboxylate urethane catalyst per 100 parts by weight polyol.

15. The composition of claim 13 which comprises a catalyst composition comprising 0.1 to 10 parts 3-methyl-3-hydroxymethyl quinuclidine and at least one other tertiary amine, organotin or metal carboxylate urethane catalyst per 100 parts by weight polyol.

16. The composition of claim 13 which comprises a catalyst composition comprising 0.1 to 10 parts 4-hydroxymethyl quinuclidine and at least one other tertiary amine, organotin or metal carboxylate urethane catalyst per 100 parts by weight polyol.

* * * * *